(12) United States Patent
Hsueh

(10) Patent No.: US 9,179,945 B2
(45) Date of Patent: Nov. 10, 2015

(54) MINIMALLY INVASIVE SPINAL FIXATOR IMPLANT SURGICAL DEVICE

(71) Applicant: Shao-Kang Hsueh, New Taipei (TW)

(72) Inventor: Shao-Kang Hsueh, New Taipei (TW)

( * ) Notice: Subject to any disclaimer, the term of this patent is extended or adjusted under 35 U.S.C. 154(b) by 175 days.

(21) Appl. No.: 13/970,614

(22) Filed: Aug. 20, 2013

(65) Prior Publication Data

US 2015/0057712 A1   Feb. 26, 2015

(51) Int. Cl.
  *A61B 17/70*  (2006.01)
  *A61B 17/00*  (2006.01)
  *A61B 17/02*  (2006.01)
  *A61B 17/34*  (2006.01)
  *A61B 19/00*  (2006.01)

(52) U.S. Cl.
  CPC ....... *A61B 17/7074* (2013.01); *A61B 17/00234* (2013.01); *A61B 17/0206* (2013.01); *A61B 17/3421* (2013.01); *A61B 19/26* (2013.01); *A61B 2017/00486* (2013.01); *A61B 2017/3405* (2013.01)

(58) Field of Classification Search
  CPC ..................... A61B 17/7074; A61B 17/00234; A61B 2017/00486; A61B 17/0206; A61B 17/3421; A61B 2017/3405; A61B 19/26
  USPC ........ 606/86 A; 600/201, 210, 215, 219, 222, 600/227–232
  See application file for complete search history.

(56) References Cited

U.S. PATENT DOCUMENTS

| 4,254,763 A | * | 3/1981 | McCready et al. | ........... 600/230 |
| 5,882,299 A | * | 3/1999 | Rastegar et al. | ............. 600/232 |
| 5,908,382 A | * | 6/1999 | Koros et al. | .................. 600/232 |
| 6,149,584 A | * | 11/2000 | Raju | ............................ 600/232 |
| 2009/0287062 A1 | * | 11/2009 | Farley | ........................... 600/231 |

\* cited by examiner

*Primary Examiner* — Pedro Philogene
*Assistant Examiner* — David C Comstock
(74) *Attorney, Agent, or Firm* — Leong C. Lei

(57) ABSTRACT

The minimally invasive spinal fixator surgical device contains a support member; a guiding member adjustably joined to the support member; at least two sliding members correspondingly and adjustably joined to the guiding member; a first extension member adjustably joined to a sliding member; a second extension member adjustably joined to another sliding member; a first pulling member joined to the first extension member; a second pulling member joined to the second extension member; a tubular member joined to a side of the first pulling member; and a probe member plugged into the tubular member for conducting implant location determination and then removed. With the assistance of the present invention, the wound and damage to the muscle tissue of the patient are minimal and there is little bleeding. The operation team is also exposed to the X-ray for a minimum amount of time. The patient would also enjoy fast recovery.

13 Claims, 5 Drawing Sheets

MINIMALLY INVASIVE SPINAL FIXATOR IMPLANT SURGICAL DEVICE

TECHNICAL FIELD OF THE INVENTION

The present invention is generally related to surgical devices, and more particular to a spinal fixator implant surgical device.

DESCRIPTION OF THE PRIOR ART

In a conventional spinal fixator implant surgery, a patient's back is cut right in the middle. Then, sequentially, skin, fascia, aponeurosis, supraspinal ligament are opened. The muscle beside the spine (i.e., multifidus) is peeled along the periosteum up to facet and transverse process, and then pulled aside by some hooks. This surgery requires that multiple tenons and ligaments attached to the spine are cut off, and that neural plate, posterior spinous process, interspinal ligament, and ligamentum flavum are removed altogether so as to reduce pressure to the nerve system. As such, some soft tissues, muscles, tenons, and ligaments are also damaged. The conventional spinal fixator implant surgery therefore has the following issues.

Firstly, after the surgery and stitching up, the patient's muscles and tenons cannot be restored to their original location, thereby damaging the physiological structure of the patient.

Secondly, dead space after the surgery is too large, thereby causing epidural fibrosis and reducing operation effect.

Thirdly, the soft tissues besides the spine are extensively cut and peeled off, thereby leading to instable spinal column.

Fourthly, a large amount of blood is lost during the surgery and massive transfusion may be required. However, the transfusion may lead to complications to the patient, such as allergy and infection.

To resolve the above issues, there are various minimally invasive surgical devices that create reduced wound and little damage by means such as internal fixation, small-cut propping, etc. However, there are still the following issues.

Firstly, these surgeries are usually required to remove intervertebral disk or to conduct extensive pressure reduction to the canalis vertebralis. However, the conventional minimal invasive surgical devices that perform only the internal fixation cannot remove intervertebral disk or conduct extensive pressure reduction at the same time.

Secondly, the surgical operators are exposed to X-ray for an extended period of time. Using only both hands to identify the fixator implant location simply adds to the operation difficulty.

Thirdly, these surgeries have a high threshold for proficiency. Lengthy professional training is required for junior operators before they can be trusted with these kinds of operations.

SUMMARY OF THE INVENTION

A major objective of the present invention is to obviate the shortcomings of the conventional spinal fixator implant surgical devices. To achieve the objective, the minimally invasive spinal fixator surgical device contains a support member; a guiding member adjustably joined to the support member; at least two sliding members correspondingly and adjustably joined to the guiding member; a first extension member adjustably joined to a sliding member where the first extension member contains a first metallic arm and a first plastic arm joined to the first metallic arm; a second extension member adjustably joined to another sliding member where the second extension member contains a second metallic arm and a second plastic arm joined to the second metallic arm; a first pulling member joined to the first plastic arm; a second pulling member joined to the second plastic arm; a tubular member joined to a side of the first pulling member; and a probe member plugged into the tubular member for conducting implant location determination and then removed.

With the minimally invasive spinal fixator surgical device, the support member can be affixed to an operating bed, and then, and by adjusting the support member, the guiding member, the sliding members, and the first and second extension members, the first and second pulling members and the tubular member are moved to the operation area of a patient. Once the implant location of the spinal fixator is determined, a surgical tool and the spinal fixator are placed in the tubular member for the subsequent implant operation. With the assistance of the present invention, the implant location can be precisely determined, the wound and damage to the muscle tissue of the patient are minimal, and there is little bleeding. The operation team is also exposed to the X-ray for a minimum amount of time.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become apparent to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
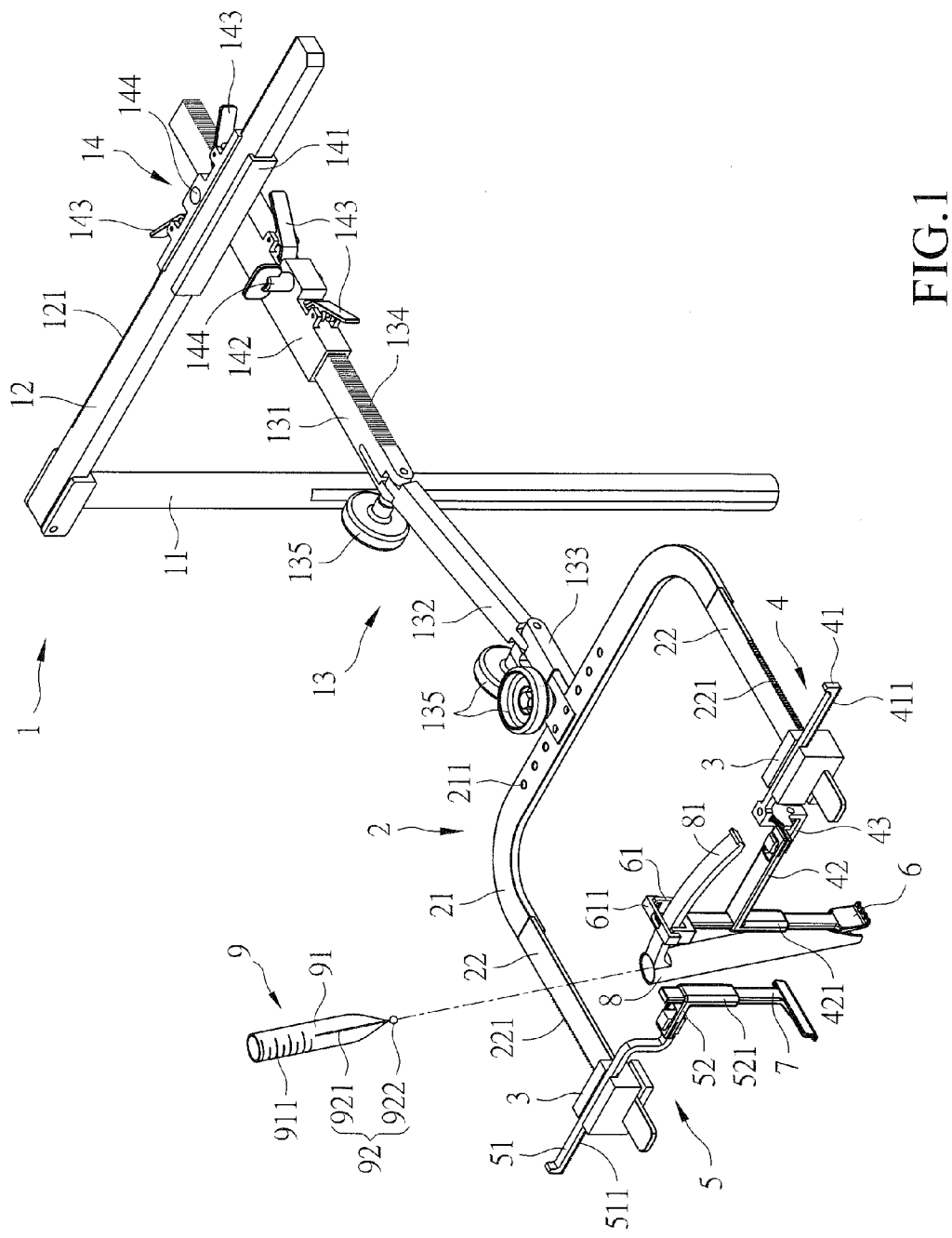
FIG. 1 is a schematic sectional diagram showing a conventional BT shank installed on a spindle assembly.
Figure 2:
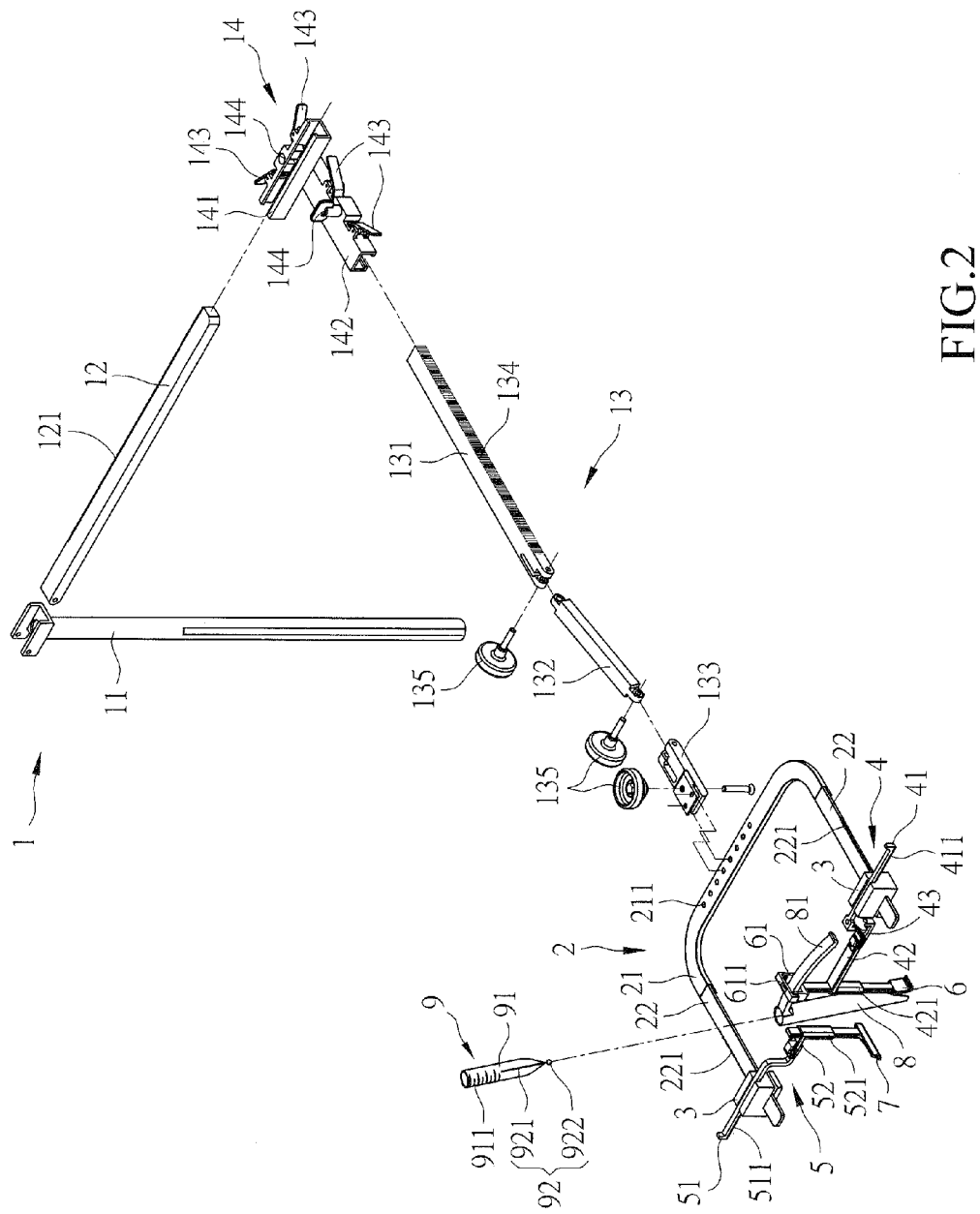
FIG. 2 is a schematic sectional diagram showing a conventional BBT shank installed on a spindle assembly.

As illustrated in FIGS. 1 and 2, a minimally invasive spinal fixator implant surgical device according to an embodiment of the present invention contains a support member 1, a guiding member 2, at least two sliding members 3, a first extension member 4, a second extension member 5, a first pulling member 6, a second pulling member 7, a tubular member 8, and a probe member 9.

The support member 1 contains a vertical column 11, a lateral beam 12, a shaft 13, and an adjustment module 14 adjustably joining the lateral beam 12 and the shaft 13. The lateral beam 12 is perpendicularly and adjustably joined to a top end of the vertical column 11 and has a sawtooth section 121 on a side of the lateral beam 12 interfering with the adjustment module 14. The shaft 13 contains a first shaft piece 131, a second shaft piece 132 pivotally joined end-to-end to an end of the first shaft piece 131 through a fastening element 135, and a third shaft piece 133 pivotally joined end-to-end to an end of the second shaft piece 132 through another fastening element 135. The first shaft piece 131 has a sawtooth section 134 on a side interfering with the adjustment module 14. The adjustment module 14 contains a beam sleeve 141 threaded by the lateral beam 12, a shaft sleeve 142 perpendicularly joined to a bottom side of the beam sleeve 141 and threaded by the first shaft piece 131 of the shaft 13. Each of the beam and shaft sleeves 141 and 142 is configured with a locking element 143 and a fastening element 144 for interfering with the sawtooth sections 121 and 134, respectively.

The guiding member 2 contains a flat main piece 21 and two flat side pieces 22 extended in parallel from the main piece 21's two ends, respectively, thereby forming a C-like shape. The guiding member 2 is adjustably joined to the shaft 13 by connecting the main piece 21 to the third shaft piece 133. The main piece 21 is configured with a number of through holes 211 and the main piece 21 is fixed to the third shaft piece 133 through yet another fastening element 135 locking into one appropriate through hole 211. Each side piece 22 has a sawtooth section 221 on a side.

Figure 3:
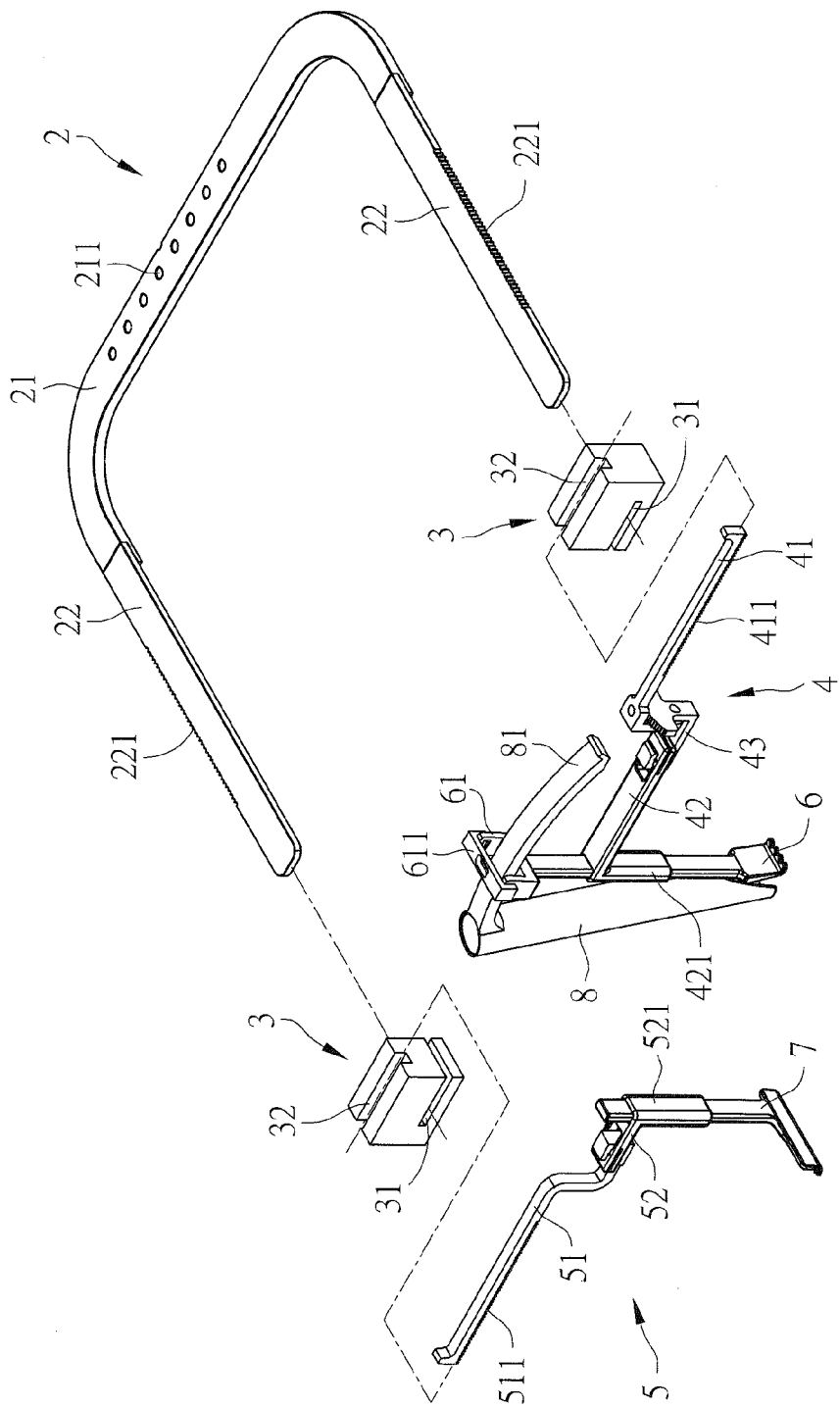
FIG. 3 is a perspective diagram of a tool shank according to a first embodiment of the present invention.

As further illustrate in FIG. 3, the sliding members 3 are correspondingly and adjustably joined to the side pieces 22, respectively. Each sliding member 3 has a slot 31 extended from a front side to a back side of the sliding member 3 so as to receive the side piece 22. Each slot 31 interferes with the sawtooth section 221 of the side piece 22. Each sliding member 3 also has a trough 32 extended from a lateral side to the other lateral side of the sliding member 3.

Figure 4:
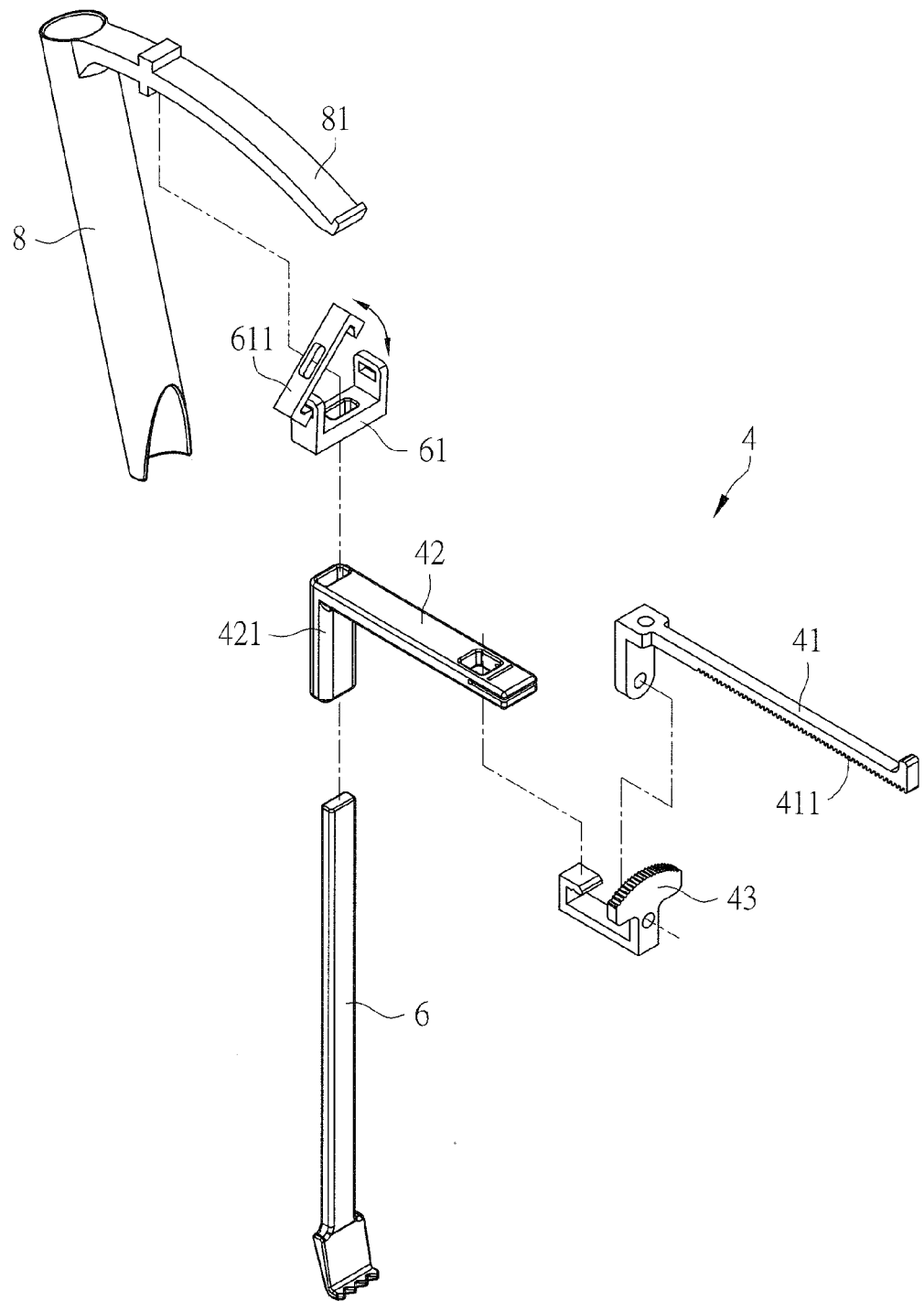
FIG. 4 a partially enlarged perspective diagram showing a number of slits on a taper member of the tool shank of FIG. 3.

As further illustrated in FIG. 4, the first extension member 4 is adjustably joined to a sliding member 3. The first extension member 4 contains a metallic arm 41 moveably received by the trough 32 of the sliding member 3 and a plastic arm 42 joined to the metallic arm 41. The metallic arm 41 has a sawtooth section 411 along a bottom side for interfering with the trough 32. An end of the plastic arm 42 has a downward extended sleeve section 421, and the other end of the plastic arm 42 is joined to the metallic arm 41 by an adjustment element 43 so that the plastic arm 42 is axially rotatably relative to the metallic arm 41.

Figure 5:
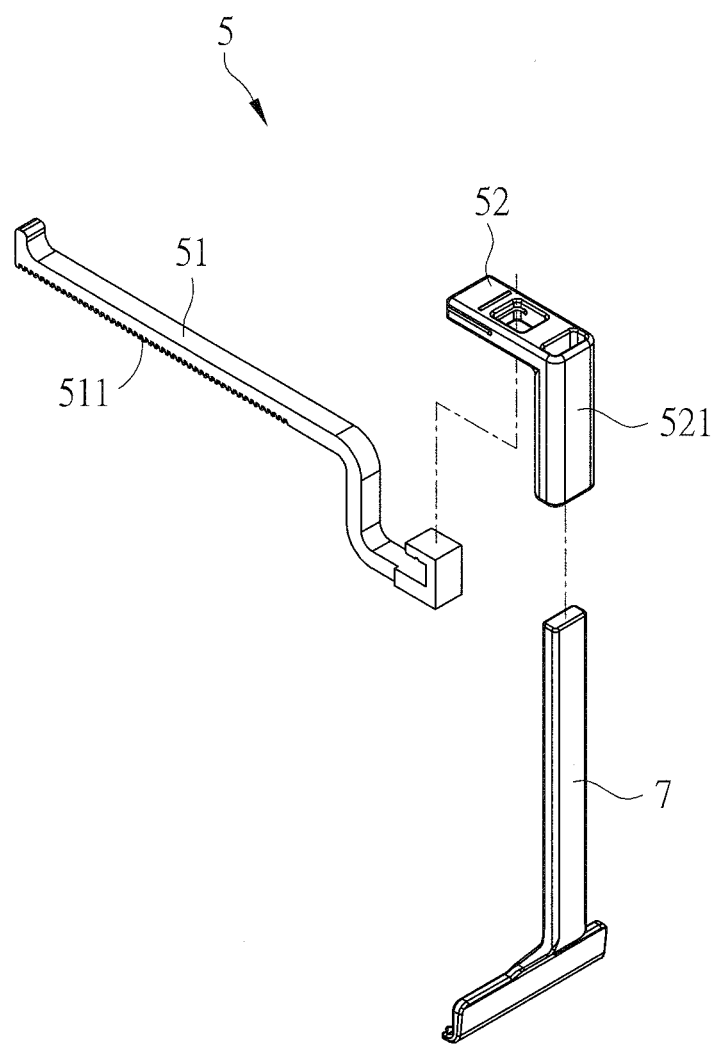
FIG. 5 is a cross-sectional diagram showing an embodiment of the slits of FIG. 4 along the V-V line of FIG. 7.

As further illustrated in FIG. 5, the second extension member 5 is adjustably joined to the other sliding member 3. The second extension member 5 contains a metallic arm 51 moveably received by the trough 32 of the sliding member 3 and a plastic arm 52 joined to the metallic arm 51. The metallic arm 51 has a sawtooth section 511 along a bottom side for interfering with the trough 32. An end of the plastic arm 42 has a downward extended sleeve section 521.

As further illustrated in FIG. 4, the first pulling member 6 is threaded through the sleeve section 421 of the first extension member 4's plastic arm 42. The first pulling member 6 has a positioning element 61 at a top end. The positioning element 61 has a cover 611 that can be closed or opened.

As further illustrated in FIG. 5, the second pulling member 7 is threaded through the sleeve section 521 of the second extension member 5's plastic arm 52.

As further illustrated in FIG. 4, the tubular member 8 is joined slantwise to a side of the first pulling member 6. A swivel arm 81 is extended laterally from a top end of the tubular member 8 adjustably through a gap between the positioning element 61 and the cover 611. The included angle between the tubular member 8 and the first pulling member 6 therefore can be adjusted between the 15 and 45 degrees.

As illustrated in FIG. 1, the probe member 9 is plugged into the tubular member 8 for conducting implant location determination. The probe member 9 is removed after the measurement is completed. The probe member 9 contains a plastic casing 91 whose circumference has a scale 911, and a metallic probe 92 extended from inside to outside of the casing 91. The metallic probe 92 contains a metallic pin 921 mostly inside the casing 91, and a metallic ball 922 outside the casing 91 on a tip of the metallic pin 91. The above described components constitute a minimally invasive spinal fixator surgical device of the present invention.

To use the minimally invasive spinal fixator surgical device, the vertical column 11 of the support member 1 can be affixed to an operating bed (not shown), and then the guiding member 2 is moved to the operation area of a patient. The position of the guiding member 2 is adjusted by shifting the first shaft piece 131 through the shaft sleeve 142 and by shifting the lateral beam 12 through the beam sleeve 141. After the guiding member 2 is at the correct position, the guiding member 2 is securely positioned by applying the locking elements 143 and the fastening elements 144 to interfere with the sawtooth sections 121 and 134, respectively. By adjusting the first, second, third shaft pieces 131, 132, 133 and the fastening element 135, the guiding member 2 can have an appropriate angle. Once the guiding member 2 is right above the operation area, the sliding members 3 are moved so that the first and second extension members 4, 5, and the first and second pulling members 6, 7 are above the operation area. When the sliding members 3 are moved, their slots 31 interfere with the sawtooth sections 221 of the side pieces 22 so that the sliding members 3 can be securely positioned. The first and pulling members 6 and 7 then are applied to pull the muscles of the operation area apart. The swivel arm 81 of the tubular member 8 is threaded through the gap between the positioning element 61 and the cover 611, and the cover 611 is closed. The tubular member 8 then is joined to a side of the first pulling member 6 with an appropriate angle. The implant location of the spinal fixator should be 15 mm vertically beneath the first pulling member 6's lowest point and should intersect the tubular member's axial direction. The tubular member 8 therefore should lie radially with the implant location as the center of a circle. The probe member 9 is then plugged into the tubular member 8. With the help of an X-ray from an operating lamp (not shown) at a side and the metallic pin 921, an exact implant location can be precisely identified. The adjustment element 43 on the metallic arm 41 of the first extension member 4 provides minor adjustment. Further with the help of a perpendicular X ray and the metallic ball 922, the implant location can be identified with enhanced precision. The first extension member 4 and the swivel arm 81 provide additional adjustment. Once the implant location is identified, the probe member 9 is retrieved, and a surgical tool and the spinal fixator are placed in the tubular member 8 for the subsequent implant operation. With the assistance of the present invention, the wound and damage to the muscle tissue of the patient are minimal and there is little bleeding. The operation team is also exposed to the X-ray for a minimum amount of time.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A minimally invasive spinal fixator surgical device, comprising:
    a support member;
    a guiding member adjustably joined to the support member;
    at least two sliding members correspondingly and adjustably joined to the guiding member;
    a first extension member adjustably joined to a sliding member, the first extension member comprising a first metallic arm and a first plastic arm joined to the first metallic arm;
    a second extension member adjustably joined to another sliding member; the second extension member comprising a second metallic arm and a second plastic arm joined to the second metallic arm;
    a first pulling member joined to the first plastic arm;
    a second pulling member joined to the second plastic arm;
    a tubular member joined to a side of the first pulling member; and
    a probe member plugged into the tubular member for conducting implant location determination and then removed;
    wherein the probe member comprises a plastic casing whose circumference has a scale, and a metallic probe extended from inside to outside of the casing; and the metallic probe comprises a metallic pin mostly inside the casing, and a metallic ball outside the plastic casing on a tip of the metallic pin.

2. The minimally invasive spinal fixator surgical device according to claim 1, wherein the support member comprises a vertical column, a lateral beam, a shaft adjustably joined to the guiding member, and an adjustment module adjustably joining the lateral beam and the shaft.

3. The minimally invasive spinal fixator surgical device according to claim 2, wherein the lateral beam is perpendicularly and adjustably joined to a top end of the vertical column and has a sawtooth section on a side of the lateral beam interfering with the adjustment module.

4. The minimally invasive spinal fixator surgical device according to claim 2, wherein the shaft comprises a first shaft piece, a second shaft piece pivotally joined end-to-end to an end of the first shaft piece, and a third shaft piece pivotally joined end-to-end to an end of the second shaft piece; the third shaft piece is adjustably joined to the guiding member; and the first shaft piece has a sawtooth section on a side interfering with the adjustment module.

5. The minimally invasive spinal fixator surgical device according to claim 4, wherein a fastening element is configured at the joints between the first shaft piece, the second shaft piece, the third shaft piece, and the guiding member.

6. The minimally invasive spinal fixator surgical device according to claim 2, wherein the adjustment module comprises a beam sleeve threaded by the lateral beam, a shaft sleeve perpendicularly joined to a bottom side of the beam sleeve and threaded by the first shaft piece of the shaft 13; and each of the beam and shaft sleeves is configured with a locking element and a fastening element for interfering with the lateral beam and the shaft, respectively.

7. The minimally invasive spinal fixator surgical device according to claim 1, wherein the guiding member comprises a flat main piece and two flat side pieces extended in parallel from the main piece 21's two ends, respectively; the main piece is adjustably joined to the support member; and each side piece has a sawtooth section on a side interfering with a sliding member.

8. The minimally invasive spinal fixator surgical device according to claim 1, wherein each sliding member has a slot extended from a front side to a back side of the sliding member so as to join to the guiding member; and each sliding member has a trough extended from a lateral side to the other lateral side of the sliding member for receiving one of the first and second extension member.

9. The minimally invasive spinal fixator surgical device according to claim 1, wherein sawtooth sections are configured along the first and second metallic arms' bottom sides, respectively.

10. The minimally invasive spinal fixator surgical device according to claim 1, wherein a sleeve section is downward extended from an end of each of the first and second plastic arms.

11. The minimally invasive spinal fixator surgical device according to claim 1, wherein the first metallic arm is joined to the first plastic arm with an adjustment element so that the plastic arm is axially rotatabe relative to the first metallic arm.

12. The minimally invasive spinal fixator surgical device according to claim 1, wherein the first pulling member has a positioning element and a cover at a top end; and a swivel arm is extended laterally from a top end of the tubular member adjustably through a gap between the positioning element and the cover.

13. The minimally invasive spinal fixator surgical device according to claim 1, wherein the tubular member is joined slantwise to a side of the first pulling member with an included angle between 15 and 45 degrees.

* * * * *